(12) United States Patent
Neoh

(10) Patent No.: US 8,657,760 B2
(45) Date of Patent: Feb. 25, 2014

(54) ERGONOMIC BIOPSY INSTRUMENT

(75) Inventor: WenHong Neoh, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 134 days.

(21) Appl. No.: 13/040,671

(22) Filed: Mar. 4, 2011

(65) Prior Publication Data

US 2012/0226191 A1 Sep. 6, 2012

(51) Int. Cl.
*A61B 10/00* (2006.01)

(52) U.S. Cl.
USPC .......... 600/562; 600/563; 600/564; 600/565; 600/566; 600/567; 600/568

(58) Field of Classification Search
USPC .......... 600/562, 564, 567, 565, 566, 568, 563
See application file for complete search history.

(56) References Cited

U.S. PATENT DOCUMENTS

| | | | |
|---|---|---|---|
| RE24,419 E | | 1/1958 | Ziherl et al. |
| 3,402,712 A | | 9/1968 | Eisenhand |
| 3,774,607 A | | 11/1973 | Schmitz |
| 3,989,033 A | * | 11/1976 | Halpern et al. ............... 600/567 |
| 4,077,406 A | | 3/1978 | Sandhage et al. |
| 4,105,030 A | | 8/1978 | Kercso |
| 4,154,239 A | | 5/1979 | Turley |
| 4,223,674 A | | 9/1980 | Fluent et al. |
| 4,400,170 A | | 8/1983 | McNaughton et al. |
| 4,447,223 A | | 5/1984 | Kaye et al. |
| 4,451,254 A | | 5/1984 | Dinius et al. |
| 4,461,305 A | * | 7/1984 | Cibley ........................ 600/567 |
| 4,667,684 A | * | 5/1987 | Leigh ......................... 600/567 |
| 4,673,387 A | | 6/1987 | Phillips et al. |
| 4,687,465 A | | 8/1987 | Prindle et al. |
| 4,699,154 A | * | 10/1987 | Lindgren .................... 600/567 |
| 4,799,921 A | | 1/1989 | Johnson et al. |
| 4,880,015 A | * | 11/1989 | Nierman ..................... 600/564 |
| 4,895,146 A | * | 1/1990 | Draenert ...................... 606/79 |
| 4,976,686 A | | 12/1990 | Ball et al. |
| 5,002,548 A | | 3/1991 | Campbell et al. |
| 5,016,614 A | * | 5/1991 | MacAllister ................ 600/131 |
| 5,127,419 A | * | 7/1992 | Kaldany ..................... 600/567 |
| 5,135,493 A | | 8/1992 | Peschke |
| 5,147,295 A | | 9/1992 | Stewart |
| 5,163,947 A | * | 11/1992 | Kvalo et al. ................. 606/151 |
| 5,213,110 A | * | 5/1993 | Kedem et al. ............... 600/567 |
| 5,250,026 A | | 10/1993 | Ehrlich et al. |
| 5,279,555 A | | 1/1994 | Lifshey |
| 5,313,958 A | * | 5/1994 | Bauer ........................ 600/567 |
| 5,320,110 A | * | 6/1994 | Wang ......................... 600/566 |
| 5,335,672 A | * | 8/1994 | Bennett ...................... 600/567 |
| 5,370,611 A | | 12/1994 | Niezink et al. |
| 5,469,860 A | * | 11/1995 | De Santis ................... 600/578 |
| 5,472,451 A | * | 12/1995 | Freitas et al. ............... 606/205 |
| 5,538,010 A | * | 7/1996 | Darr et al. .................. 600/567 |

(Continued)

FOREIGN PATENT DOCUMENTS

JP 08019507 A * 1/1996

*Primary Examiner* — Jeffrey G Hoekstra
*Assistant Examiner* — May Abouelela
(74) *Attorney, Agent, or Firm* — Buchanan Nipper

(57) ABSTRACT

Biopsy instruments having an ergonomic design are described. A biopsy instrument comprises a housing, a needle assembly, and a handle. The needle assembly includes a cannula that defines a lumen and a stylet slidably disposed within the lumen. The housing and the handle have longitudinal axes that intersect at an acute angle.

19 Claims, 5 Drawing Sheets

(56) References Cited

U.S. PATENT DOCUMENTS

| | | | |
|---|---|---|---|
| 5,702,349 A * | 12/1997 | Morizumi | 600/131 |
| 5,817,033 A * | 10/1998 | DeSantis et al. | 600/562 |
| 5,817,054 A | 10/1998 | Grimm | |
| 5,830,153 A * | 11/1998 | Kass | 600/567 |
| 5,857,982 A * | 1/1999 | Milliman et al. | 600/567 |
| 5,868,785 A * | 2/1999 | Tal et al. | 606/207 |
| 5,921,943 A * | 7/1999 | Kass | 600/567 |
| 5,957,863 A * | 9/1999 | Koblish et al. | 600/567 |
| 5,997,485 A * | 12/1999 | Ahmadzadeh | 600/567 |
| 6,190,350 B1 | 2/2001 | Davis et al. | |
| 6,213,957 B1 * | 4/2001 | Milliman et al. | 600/566 |
| 6,280,398 B1 * | 8/2001 | Ritchart et al. | 600/564 |
| 6,398,741 B2 * | 6/2002 | Niizeki et al. | 600/566 |
| 6,530,125 B2 * | 3/2003 | Shippert | 16/430 |
| 6,702,760 B2 * | 3/2004 | Krause et al. | 600/564 |
| 6,976,968 B2 * | 12/2005 | Ritchart et al. | 600/567 |
| 7,169,114 B2 * | 1/2007 | Krause | 600/564 |
| D536,792 S | 2/2007 | Krueger | |
| 7,214,206 B2 | 5/2007 | Rue et al. | |
| 7,458,940 B2 * | 12/2008 | Miller | 600/568 |
| 7,468,041 B2 * | 12/2008 | Rhodes et al. | 600/564 |
| 7,794,411 B2 * | 9/2010 | Ritchart et al. | 600/567 |
| 7,914,463 B2 * | 3/2011 | Tarter et al. | 600/567 |
| 2001/0005778 A1 * | 6/2001 | Ouchi | 600/564 |
| 2004/0133124 A1 | 7/2004 | Bates et al. | |
| 2004/0158172 A1 * | 8/2004 | Hancock | 600/564 |
| 2004/0249278 A1 * | 12/2004 | Krause | 600/435 |
| 2007/0055173 A1 * | 3/2007 | DeLonzor et al. | 600/564 |
| 2007/0123797 A1 * | 5/2007 | Krause | 600/562 |
| 2007/0167868 A1 * | 7/2007 | Sauer | 600/564 |
| 2007/0208272 A1 * | 9/2007 | Voegele | 600/564 |
| 2009/0318830 A1 * | 12/2009 | George et al. | 600/564 |
| 2010/0049087 A1 * | 2/2010 | Spero et al. | 600/567 |
| 2010/0160824 A1 * | 6/2010 | Parihar et al. | 600/567 |
| 2011/0028976 A1 * | 2/2011 | Miller | 606/79 |

* cited by examiner

ERGONOMIC BIOPSY INSTRUMENT

FIELD

The invention relates generally to the field of medical devices. More particularly, the invention relates to instruments useful in the performance of tissue biopsy. The invention also relates to tissue biopsy methods.

BACKGROUND

Biopsy is the removal and study of body tissue from a body for medical diagnosis, research or for other purposes. For example, clinicians frequently remove biopsy samples from patients to screen for the existence of a disease condition, such as cancer, and to determine the extent to which the disease condition has spread throughout the body. The art provides various biopsy instruments useful in acquiring tissue samples from different areas of the body.

Currently available biopsy instruments typically comprise a two-part needle assembly in which a cutting cannula surrounds a stylet that defines a specimen notch. In use, a spring mechanism initially advances the stylet into a target tissue to force a core tissue sample into the specimen notch, and then advances the cannula over the specimen notch to separate the core sample from the surrounding tissue. The user then removes the biopsy instrument and the core sample it contains from the body. An example of this type of instrument is described in U.S. Pat. No. 5,538,010 to Darr et al. for a BIOPSY NEEDLE ASSEMBLY DEVICE, the entire disclosure of which is incorporated herein by reference.

Another exemplary biopsy instrument is the QUICK-CORE® Biopsy Needle assembly available from Cook Incorporated. In this instrument, each of the stylet and the cannula defines a series of notches that impart flexibility onto the instrument, facilitating its navigation through tortuous anatomy. This instrument is described and illustrated in Unites States Patent Application Publication No. 2004/0133124 to Bates et al. for a FLEXIBLE BIOPSY NEEDLE ASSEMBLY.

Several currently available soft tissue biopsy needle assemblies utilize an in-line-type handle on the proximal end of the device for the main body of the instrument. These handles offer limited control over inserting and guiding the biopsy needle assembly into the patient because they force the user to arrange their hand that holds the instrument into an open palm, supine position. This position can be uncomfortable and can even place a strain on the user's hand(s), finger(s), and/or wrist. Furthermore, these handles also can force the user to contract their index and/or middle finger as they use their other hand to advance the needle assembly tip into the biopsy area. This unintended finger contraction can move the biopsy needle assembly out of alignment with the biopsy area, which may result in the core sample being removed from tissue that is spaced from the target tissue.

SUMMARY

Several exemplary biopsy instruments are described herein. The instruments are useful in the performance of tissue biopsy on various tissues in a variety of animals, including soft and other tissues of human beings.

Biopsy instruments having an ergonomic design are described. The instruments offer improved control and precision over currently available instruments during insertion of the needle assembly into the target tissue. The instruments also provide the user with improved control over currently available instruments during release of the cutting cannula so that the position of the needle assembly is not compromised and the sample is removed from the intended target tissue.

An exemplary biopsy instrument comprises a housing, a needle assembly, and a handle. The needle assembly includes a cannula that defines a lumen and a stylet slidably disposed within the lumen. The housing and the handle have longitudinal axes that intersect at an angle, such as an acute angle.

Another exemplary biopsy instrument comprises a housing having a front end opposite a rear end and a housing length extending between the front end and the rear end. The housing has a first longitudinal axis extending along the housing length and defines an inner passageway. A needle assembly extends from the front end of the housing and has a proximal end disposed in the inner passageway of the housing. The needle assembly includes a cannula that defines a lumen and a stylet slidably disposed within the lumen. The distal end of the stylet defines a specimen notch adapted to receive a core sample of tissue during use of the biopsy instrument in a biopsy method. The biopsy instrument also includes a support shaft that is moveable between a chambered position in which the support shaft is substantially disposed within the inner passageway of the housing and a retracted position in which the support shaft is substantially retracted from the inner passageway. The support shaft is operably connected to the stylet and the cannula such that proximally-directed movement of the support shaft from the chambered position to the retracted position and along the longitudinal axis of the housing produces proximally-directed movement of the stylet and the cannula along the first longitudinal axis. Distally-directed movement of the support shaft from the retracted position to the chambered position and along the first longitudinal axis produces distally-directed movement of the stylet. A handle is connected to the housing and extends away from the housing. The handle has a second longitudinal axis that intersects the first longitudinal axis at an acute angle.

Another exemplary biopsy instrument comprises a housing having a front end opposite a rear end and a housing length extending between the front end and the rear end. The housing has a first longitudinal axis extending along the housing length and defines an inner passageway. A needle assembly extends from the front end of the housing and has a proximal end disposed in the inner passageway of the housing. The needle assembly includes a cannula that defines a lumen and a stylet slidably disposed within the lumen. The distal end of the stylet defines a specimen notch adapted to receive a core sample of tissue during use of the biopsy instrument in a biopsy method. The biopsy instrument also includes a support shaft that is moveable between a chambered position in which the support shaft is substantially disposed within the inner passageway of the housing and a retracted position in which the support shaft is substantially retracted from the inner passageway. The support shaft is operably connected to the stylet and the cannula such that proximally-directed movement of the support shaft from the chambered position to the retracted position and along the longitudinal axis of the housing produces proximally-directed movement of the stylet and the cannula along the first longitudinal axis. Distally-directed movement of the support shaft from the retracted position to the chambered position and along the first longitudinal axis produces distally-directed movement of the stylet. A priming slider is connected to the housing and the support shaft and is such that movement of the priming slider from a first position to a second position results in movement of the support shaft from the chambered position to the retracted position. A handle is connected to the housing and extends away from the housing. The handle has a second longitudinal axis that intersects the first longitudinal axis at an acute angle.

Another exemplary biopsy instrument comprises a housing having a front end opposite a rear end and a housing length extending between the front end and the rear end. The housing has a first longitudinal axis extending along the housing length and defines an inner passageway. A needle assembly extends from the front end of the housing and has a proximal end disposed in the inner passageway of the housing. The needle assembly includes a cannula that defines a lumen and a stylet slidably disposed within the lumen. The distal end of the stylet defines a specimen notch adapted to receive a core sample of tissue during use of the biopsy instrument in a biopsy method. The biopsy instrument also includes a support shaft that is moveable between a chambered position in which the support shaft is substantially disposed within the inner passageway of the housing and a retracted position in which the support shaft is substantially retracted from the inner passageway. The support shaft is operably connected to the stylet and the cannula such that proximally-directed movement of the support shaft from the chambered position to the retracted position and along the longitudinal axis of the housing produces proximally-directed movement of the stylet and the cannula along the first longitudinal axis. Distally-directed movement of the support shaft from the retracted position to the chambered position and along the first longitudinal axis produces distally-directed movement of the stylet. A priming slider is connected to the housing and the support shaft and is such that movement of the priming slider from a first position to a second position results in movement of the support shaft from the chambered position to the retracted position. A gripping portion is disposed on the front end of the housing and is configured for grasping by an operator of the biopsy instrument. A handle is connected to the housing and extends away from the housing. The handle has a second longitudinal axis that intersects the first longitudinal axis at an acute angle.

Additional understanding of the devices and methods contemplated and/or claimed by the inventor can be gained by reviewing the detailed description of exemplary devices and methods, presented below, and the referenced drawings.

DETAILED DESCRIPTION

Figure 1:
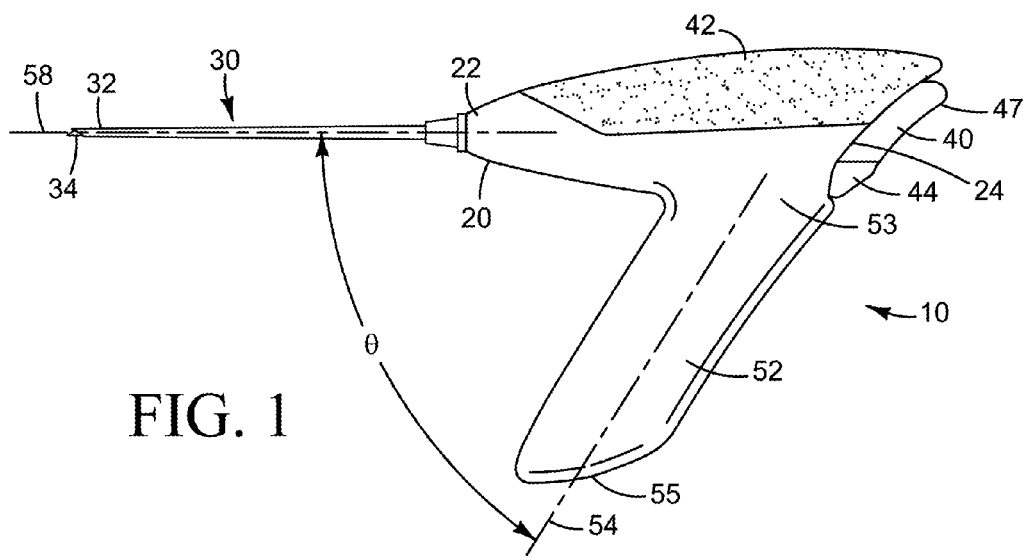
FIG. 1 is a side view of a first exemplary biopsy instrument.

The following description and the referenced drawings provide illustrative examples of that which the inventor regards as his invention. As such, the embodiments discussed herein are merely exemplary in nature and are not intended to limit the scope of the invention, or its protection, in any manner. Rather, the description and illustration of these embodiments serve to enable a person of ordinary skill in the relevant art to practice the invention.

As used herein, the terms "e.g.," "etc.," and "or" indicate non-exclusive alternatives without limitation unless otherwise noted. Also, the term "including" and grammatically related terms means "including, but not limited to," unless otherwise noted.

Ergonomic biopsy instruments are disclosed. The instruments include a handle that extends away from the longitudinal axis of the instrument at an angle. In exemplary embodiments, the handle extends away from the longitudinal axis at a slight forward angle, toward the front or needle assembly-side of the instrument.

FIGS. 1, 5A, 5B, 5C, 5D, 5E and 5F illustrate a first exemplary biopsy instrument 10. The instrument 10 comprises a housing 20 and a needle assembly 30.

The housing 20 has a front end 22 opposite a rear end 24 and defines a housing length extending between the front 22 and rear 24 ends. The housing 20 has a longitudinal axis 58 defined generally along the housing length. In this embodiment, the needle assembly 30 is positioned generally along and is substantially aligned with the longitudinal axis 58.

The needle assembly 30 extends outward and away from the front end 22 of the housing 20. The needle assembly 30 comprises a cannula 32 and a stylet 34. The stylet 34 has a proximal end (not illustrated in the figures) and a distal end 38. The proximal end is connected to a support shaft 40 that is slidably disposed within a passageway defined by the housing 20, as described in more detail below. The cannula 32 is disposed over and surrounds the stylet 34 such that the stylet 34 is slidably disposed within the cannula 32.

A handle 52 extends from the housing 20 and defines a grip suitable for grasping by the hand of a user. In this embodiment, the handle 52 extends substantially from the rear end 24 of the housing 20. The handle 52 has a housing end 53 opposite a butt end 55 and defines a handle length extending between the housing 53 and butt 55 ends. The handle 52 has a longitudinal axis 54 defined generally along the handle length.

The housing end 53 of the handle 52 is connected to the housing 20. In this embodiment, the housing end 53, and indeed the entire handle 52, is integrally formed with the housing 20.

As best illustrated in FIG. 1, the longitudinal axis 54 of the handle 52 and the longitudinal axis 58 of the housing 20 intersect one another at an angle represented by the Greek letter theta (Θ). Any suitable angle can be used for angle Θ, and skilled artisans will be able to select an appropriate angle for use in a biopsy instrument according to a specific embodiment based on various considerations, including the overall size of the biopsy instrument, the tissue from which the instrument will be used for removing samples, and other considerations. Examples of suitable angles for angle Θ include acute and obtuse angles. The inventor has determined that an acute angle for angle Θ provides a desired degree of control over biopsy instruments at least because such an angle extends the butt end 55 of the handle 52 toward the front end 22 of the housing 20. This orientation and arrangement of the structural elements is considered advantageous at least because it places a user's hand into a grip in which one or more fingers can readily be extended over the front end 22 of the housing 20 and the thumb can be retracted and advanced to effect advancement of the stylet 34 and/or cannula 32 without forcing the other four fingers to contract or otherwise move from their position on the front end 22 of the housing 20 or from their position on the handle 52. This is believed to be advantageous at least because it is expected to reduce and/or eliminate the unintended finger contraction associated with prior art biopsy instruments that can move the biopsy needle assembly out of alignment with the intended biopsy area, which may result in the core sample being removed from tissue that is spaced from the target tissue.

The inventor has determined that an acute angle greater than about 0° but less than about 90° for angle Θ provides a desired degree of control over the biopsy needle assembly. Suitable acute angles for angle Θ include an angle greater than about 40° but less than about 85°, an angle greater than about 45° but less than about 80°, an angle greater than about 50° but less than about 75°, an angle greater than about 55° but less than about 75°, an angle greater than about 60° but less than about 75°, and an angle greater than about 60° but less than about 70°. The inventor has determined that an angle of about 55° for angle Θ provides a desired degree of control over biopsy instruments intended for use in deep soft tissue biopsy methods. The inventor has determined that an angle of about 60° for angle Θ also provides a desired degree of control over biopsy instruments intended for use in deep soft tissue biopsy methods. The inventor has determined that an angle of about 65° for angle Θ also provides a desired degree of control over biopsy instruments intended for use in deep soft tissue biopsy methods.

The inventor has determined that an acute angle for angle Θ allows a user to grip and manipulate the biopsy instrument 10 in a manner that is generally more comfortable for humans than the manner in which prior art biopsy instruments are gripped and/or manipulated. Thus, an acute angle for angle Θ is considered advantageous at least because it confers an ergonomic configuration onto the biopsy instrument and is expected to reduce and/or eliminate the finger, hand, and/or wrist strain frequently associated with the holding, manipulating, and operating of prior art biopsy instruments. Furthermore, an acute angle and the angles and ranges of angles listed above are considered to be advantageous at least because such angles position the hand, wrist, and digits of a user into a configuration that allows the user to apply a greater pushing force onto the biopsy instrument 10 during priming, insertion, and other operations of the biopsy instrument 10. Additionally, an acute angle and the angles and ranges of angles listed above are considered to be advantageous at least because, in normal use, a user pushes a biopsy instrument across the frontal plane of their body as they stand perpendicular to a patient lying on a bed or other support. An acute angle and the angles and ranges of angles listed above place the user's hand into a configuration that facilitate such a pushing motion across the user's body.

Figure 5A:
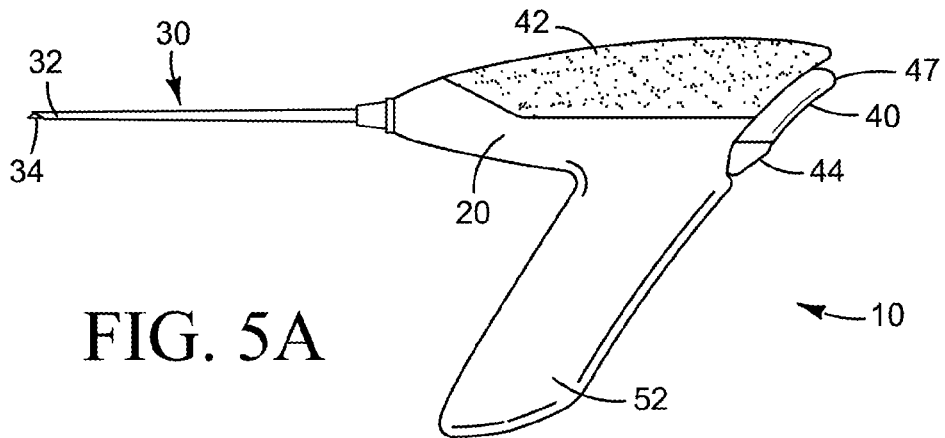
FIG. 5A is a side view of the biopsy instrument illustrated in FIG. 1 in a first configuration.
Figure 5B:
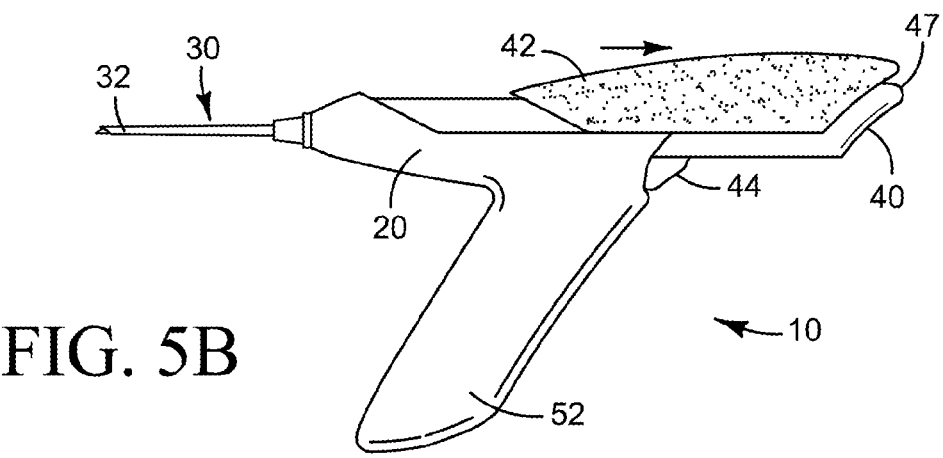
FIG. 5B is a side view of the biopsy instrument illustrated in FIG. 1 in a second configuration.

A priming slider 42 is operably connected to the housing 20 such that the priming slider 42 is movable between a first position in which the priming slider 42 is disposed substantially over the housing 20 (illustrated in FIGS. 1 and 5A) to a second position in which the priming slider 42 is extended along the longitudinal axis 58 away from the rear end 24 of the housing 20 (illustrated in FIG. 5B). In this embodiment, the priming slider 42 is biased to the first position, such as by inclusion of at least one spring that places a spring bias on the priming slider 42. This arrangement is considered advantageous at least because it forces the priming slider 42 to return automatically to the first position after a user has moved the priming slider 42 to the second position and released the priming slider 42. Alternatively, the priming slider 42 can be free of any bias toward either of the first and second positions.

As described more fully below, a user grasps the handle 52 with one hand and the priming slider 42 with the other hand to prepare the biopsy instrument for use. The user can then move the priming slider 42 proximally from the first position to the second position and along the longitudinal axis 58 of the housing 20. Such movement of the priming slider 42 forces the support shaft 40 to move from a chambered position, illustrated in FIG. 5A, in which the support shaft 40 is substantially disposed within the passageway defined by the housing 20 to a retracted position, illustrated in FIG. 5B, in which the support shaft 40 is extended along the longitudinal axis 58 away from the rear end 24 of the housing 20. As described above, the proximal end of the stylet 34 (not shown in the figures) is attached to the support shaft 40. As a result, this proximal movement of the support shaft 40 from the chambered position to the retracted position forces the stylet 34 to move along the longitudinal axis 58 of the biopsy instrument such that a portion of the stylet 34 is retracted into the passageway defined by the housing 20, as illustrated in FIG. 5B. In this position, the distal end of the cannula 32 extends over the distal end 38 of the stylet 32. Also, the cannula 32 can be locked in a ready-to-fire position, as described in more detail below.

Figure 5C:
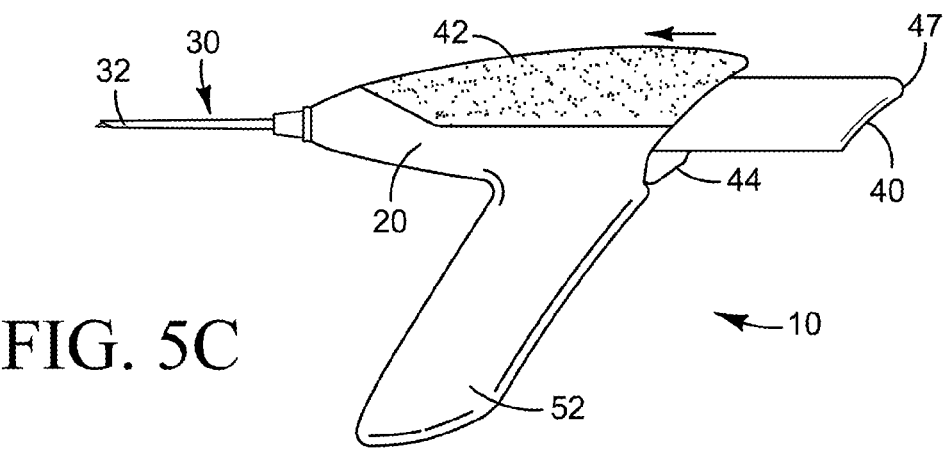
FIG. 5C is a side view of the biopsy instrument illustrated in FIG. 1 in a third configuration.
Figure 5D:
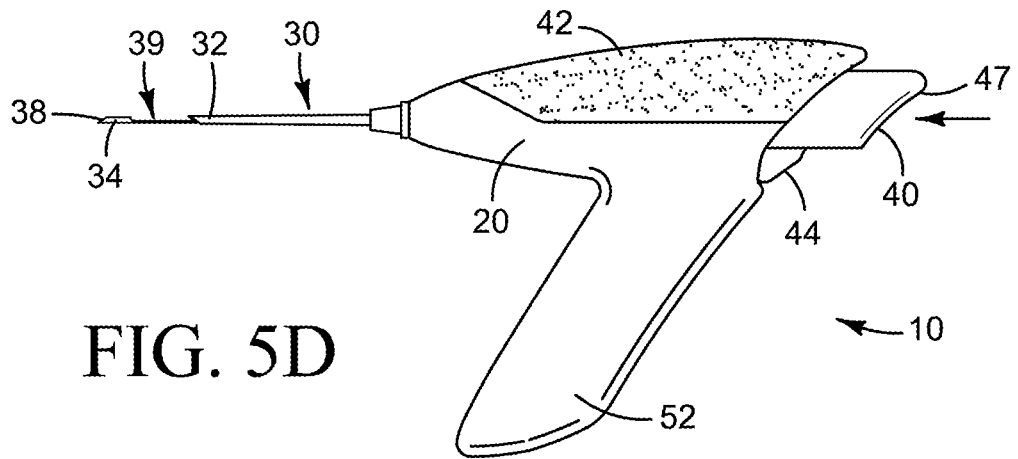
FIG. 5D is a side view of the biopsy instrument illustrated in FIG. 1 in a fourth configuration.
Figure 5E:
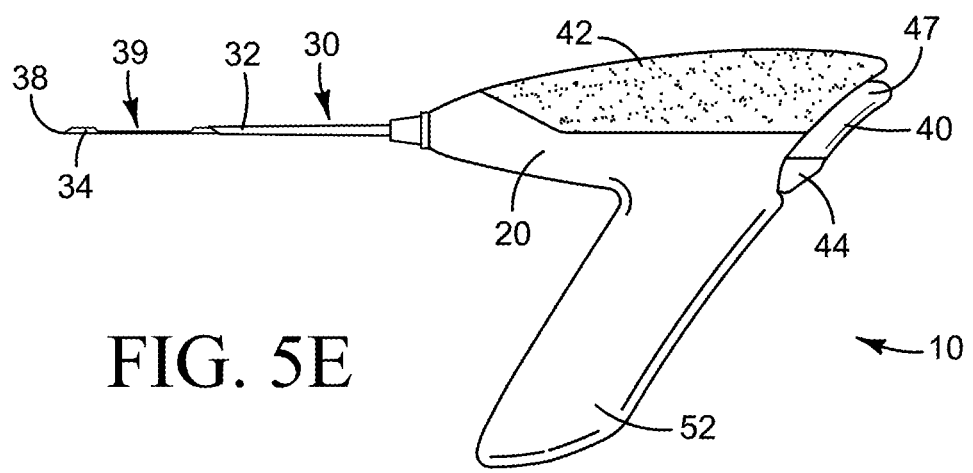
FIG. 5E is a side view of the biopsy instrument illustrated in FIG. 1 in a fifth configuration.

After the priming slider 42 has been moved into the second position, placing the support shaft 40 into the retracted position, a user can advance the support shaft 40 distally to return the support shaft 40 to the chambered position (illustrated in FIG. 5E). Similar to the first movement described above, the attachment of the proximal end of the stylet 34 to the support shaft forces the distal end 38 of the stylet 34 out of the distal end of the cannula 32 as a result of this movement of the support shaft 40. This movement is illustrated in FIGS. 5C, 5D and 5E. The specimen notch 39 defined by the stylet 34 is exposed as a result (see FIGS. 5D and 5E, for example).

The support shaft 40 has an inner end that is connected to the proximal end of the stylet 34, and an outer end that extends away from and out of the housing 20. The outer end is configured for manipulation by a user as described above. Any suitable structure can be used for the outer end of the support shaft 40 and a skilled artisan will be able to select suitable structure for inclusion in a biopsy instrument according to a particular embodiment based on various considerations, including the handedness of the intended user, the size of the hands and/or fingers of the intended user, and other considerations. In the illustrated embodiment, the outer end of the support shaft 40 defines a plunger head 47 that can be depressed or otherwise manipulated by the user to advance the support shaft 40 as described above. In this embodiment, the plunger head 47 defines a recessed surface adapted to receive a thumb or other digit of a user.

Figure 5F:
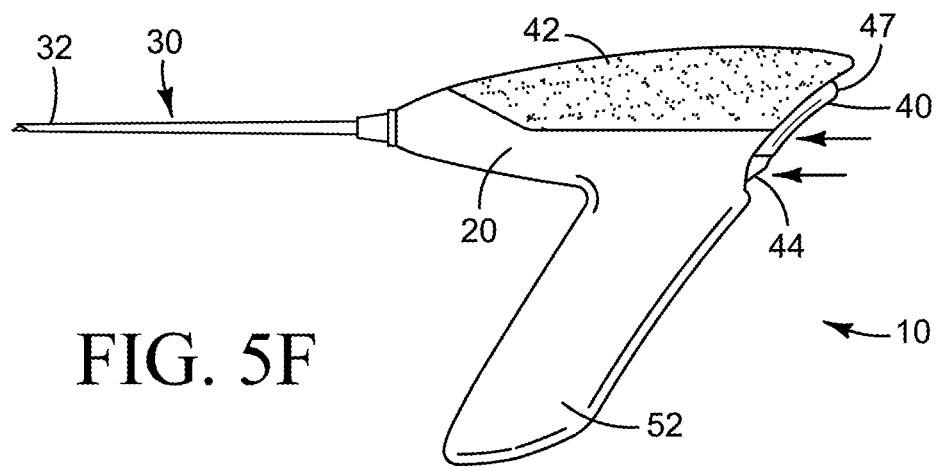
FIG. 5F is a side view of the biopsy instrument illustrated in FIG. 1 in a sixth configuration.

In this embodiment, a spring is disposed within the housing and is operably connected to the priming slider 42 such that movement of the priming slider 42 from the first position to the second position forces the cannula 32 to compress the spring. When the priming slider 42 is in the second position, the cannula 32 is held in a spring-biased ready position in which the cannula 32 is ready to be fired. Once in this position, the cannula 32 can be selectively released and quickly moved proximally into a sampling position (as illustrated in FIG. 5F).

In this embodiment, a firing trigger 44 is disposed adjacent the plunger head 47 of the support shaft 40 and is operably connected to the spring. Depression of the firing trigger 44 releases the spring from its compressed position, allowing the spring to release its stored energy and advance the cannula 32 proximally relative to the stylet 34. As a result of this movement, the cannula 32 is advanced over the stylet 34 such that the cutting edge defined by the distal end of the cannula 32 separates tissue stored in the specimen notch 39 of the stylet 34 from the surrounding tissue. The user can then retract the biopsy instrument 10 to extract the biopsy sample from the body.

The arrangement of the firing trigger 44 below the priming slider 42 and the plunger head 47 of the support shaft 40 provides a safety feature that protects against accidental premature depression of the firing trigger 44 before the cutting cannula 32 is fully extended and positioned in the desired position within the tissue. Specifically, as best illustrated in FIGS. 5B, 5C, and 5D, the priming slider 42, when in the second position, is positioned over the firing trigger 44, effectively shielding the firing trigger 44 and blocking contact with it by the user's hand and other potential triggering contact. Similarly, the support shaft 40, when in the retracted position, is also positioned over the firing trigger 44 and provides a similar shielding effect.

Figure 2:
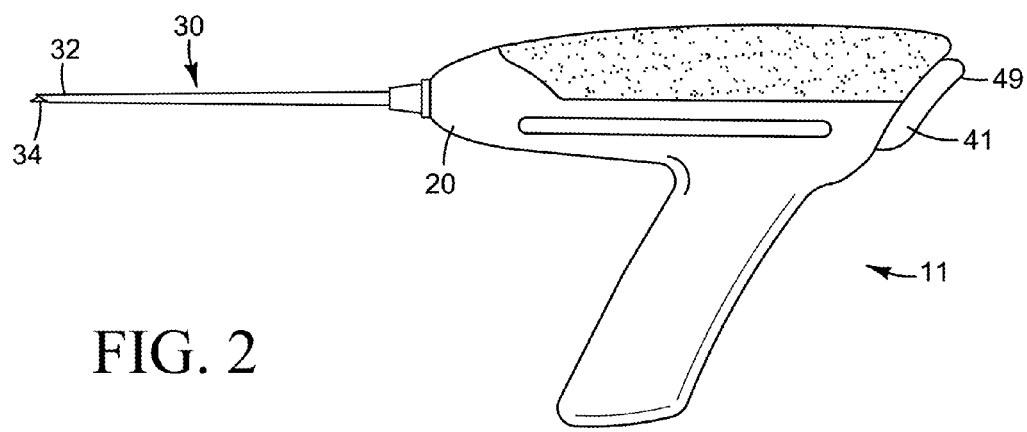
FIG. 2 is a side view of a second exemplary biopsy instrument.

FIG. 2 illustrates a second exemplary biopsy instrument 11. The biopsy instrument 11 is similar to the biopsy instrument 10 illustrated in FIG. 1 and described above, except as detailed below. Thus, the biopsy instrument includes a housing 20 and a needle assembly 30 comprising an outer cannula 32 disposed around an inner stylet 34.

In this embodiment, the support shaft 41 is used to both advance the stylet 34 and for firing the cutting cannula 32. Thus, a separate firing trigger is not included in the biopsy instrument 11. The outer end of the support shaft 41 defines a plunger head 49 that can be depressed or otherwise manipulated by the user to advance the support shaft 41. In use, the support shaft 41 is adapted to advance the stylet 34 when moved distally from a retracted position to an intermediate position. Continued distally-directed movement of the support shaft 41 past the intermediate position releases the spring from its compressed position, allowing the spring to release its stored energy and advance the cannula 32 proximally relative to the stylet 34. As a result of this movement, the cannula 32 is advanced over the stylet 34 such that the cutting edge defined by the distal end of the cannula 32 separates tissue stored in the specimen notch (not illustrated in FIG. 2) of the stylet 34 from the surrounding tissue. The user can then retract the biopsy instrument 11 to extract the biopsy sample from the body.

Figure 3:
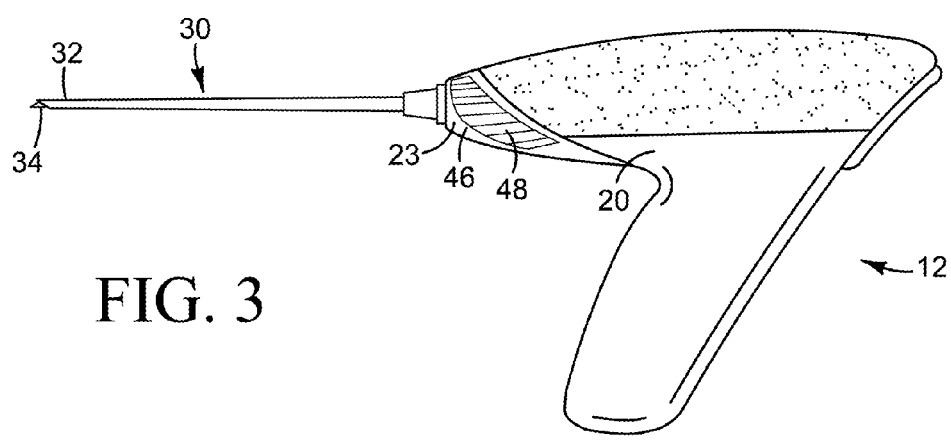
FIG. 3 is a side view of a third exemplary biopsy instrument.

FIG. 3 illustrates a third exemplary biopsy instrument 12. The biopsy instrument 12 is similar to the biopsy instrument 10 illustrated in FIG. 1 and described above, except as detailed below.

In this embodiment, the housing 20 has a front end 23. A finger grip portion 46 that defines a surface configured for secure gripping of the biopsy instrument 12 is connected to the front end 23. A user can hold the biopsy instrument 12 by gripping the finger grip portion 46 between his/her index finger and thumb while bracing the handle 52 within the palm of their hand. In this position, the user can manipulate the biopsy instrument 12 by moving only the gripping fingers and/or by only slightly moving his/her wrist. The inclusion of the finger grip portion 46 is considered advantageous at least because it facilitates control of the biopsy instrument 12 in this manner, which is believed to be advantageous at least during the steps of inserting the primed biopsy instrument into the patient and advancing the needle assembly of the primed biopsy instrument to the desired depth in the target tissue, as described more fully below.

Any suitable structure and/or material can be used for the finger grip portion 46, and a skilled artisan will be able to select an appropriate structure and material for the finger grip portion 46 in a particular embodiment based on various considerations, including the intended use of the biopsy instrument, the intended arena within which the biopsy instrument will be used, and the equipment and/or accessories with which the biopsy instrument is intended to be used, among other considerations. As illustrated in FIG. 3, the inventor has determined that a grip that defines a series of raised ribs 48 provides a suitable structure for the finger grip portion 46. Also, a rubber material formed with conventional techniques, such as overmolding, is considered suitable for use in biopsy instruments intended to be operated by bare hands and/or by hands gloved in conventional latex gloves.

Figure 4:
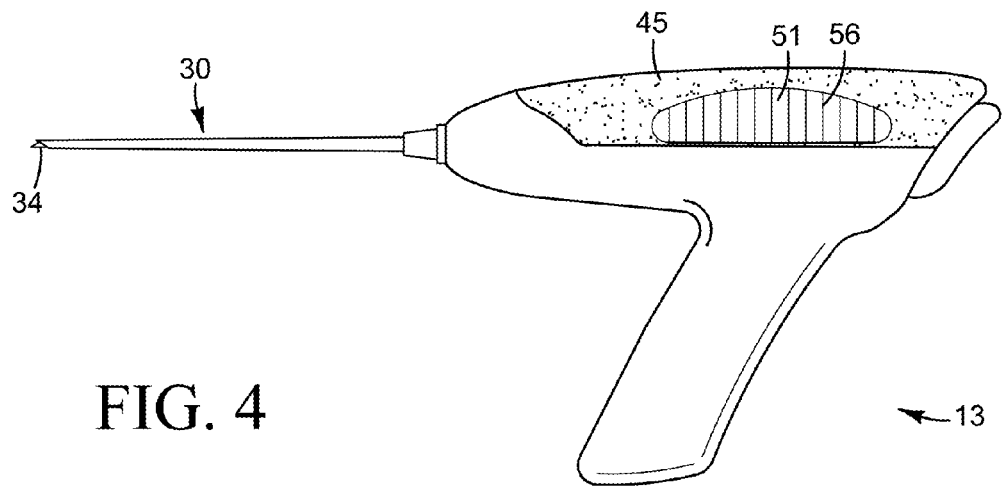
FIG. 4 is a side view of a fourth exemplary biopsy instrument.

FIG. 4 illustrates a fourth exemplary biopsy instrument 13. The biopsy instrument 13 is similar to the biopsy instrument 10 illustrated in FIG. 1 and described above, except as detailed below.

In this embodiment, a priming slider grip portion 51 is attached to the priming slider 45. The priming slider grip portion 51 defines a surface configured for secure gripping of the priming slider 45 by a user during its movement from the first position to the second position.

Any suitable structure and/or material can be used for the priming slider grip portion 51, and a skilled artisan will be able to select an appropriate structure and material for the priming slider grip portion 51 in a particular embodiment based on various considerations, including the intended use of the biopsy instrument, the intended arena within which the biopsy instrument will be used, and the equipment and/or accessories with which the biopsy instrument is intended to be used, among other considerations. As illustrated in FIG. 4, the inventor has determined that a grip that defines a series of raised ribs 56 provides a suitable structure for the priming slider grip portion 51. The inventor has also determined that a priming slider grip portion 51 that defines a concave surface and that includes a series of raised ribs 56 is particularly suitable for biopsy instruments intended for use in deep soft tissue biopsy methods. Also, a rubber material formed with conventional techniques, such as overmolding, is considered suitable for use in biopsy instruments intended to be operated by bare hands and/or by hands gloved in conventional latex gloves.

It is noted that all structure and features of the various described and illustrated embodiments can be combined in any suitable configuration for inclusion in a biopsy instrument according to a particular embodiment. For example, a biopsy instrument according a particular embodiment can include neither, one, or both of the finger grip portion 46 and the priming slider grip portion 51 described above. Furthermore, a biopsy instrument according to a particular embodiment can include either the support shaft 40 and firing trigger 44 described above or the alternative support shaft 41 in combination with neither, one, or both of the finger grip portion 46 and the priming slider grip portion 51 described above.

Any suitable materials can be used to form the various components of the biopsy instruments, and a skilled artisan will be able to select appropriate materials for a biopsy instrument according to a particular embodiment based on various considerations, including the tissue within which the biopsy instrument is intended to be used, the environment within which the biopsy instrument is intended to be used, and the sterilization parameters and/or sterilants to which the biopsy instrument is intended to be exposed. The inventor has determined that conventional polymeric and metal materials are suitable for use in the various components of the biopsy apparatus. For example, the housing and associated components can be injection-molded from suitable plastics known in the art. The stylet and cutting cannula can be formed from metal materials, including stainless steel and other suitable metals. Materials hereinafter discovered and/or developed that are determined to be suitable for use in invasive medical devices would also be considered suitable for use in a biopsy instrument according to a particular embodiment.

FIGS. 5A through 5E illustrate, sequentially, the biopsy instrument 10 in FIG. 1 in various configurations adopted during use.

FIG. 5A illustrates the biopsy instrument 10 in an initial configuration. In this configuration, the priming slider 42 is in the first position and the support shaft 40 is in the chambered position. As a result, the cannula 32 is extended over the stylet (not visible in FIG. 5A). This is the configuration within which the biopsy instrument 10 will typically be disposed prior to its use in a biopsy method.

FIG. 5B illustrates the biopsy instrument 10 in a second configuration. In this configuration, the priming slider 42 has been moved proximally from the first position to the second position, as represented by the arrow, which has forced the support shaft 40 and the needle assembly 30 also to move proximally. In this configuration, the support shaft 40 is in its retracted position. The firing trigger 44 remains in the position it occupied in the initial configuration, but is now poised to release the energy stored in the spring by its compression caused by the movement of the priming slider 42 from the first position to the second position.

FIG. 5C illustrates the biopsy instrument 10 in a third configuration. In this configuration, the priming slider 42 has returned to its first position after the user has removed his grip on the priming slider 42. As described above, this return movement can occur automatically upon release of the user's grip on the priming slider 42 in embodiments in which the priming slider 42 is biased toward its first position. This configuration is referred to as the "primed" or "cocked" configuration of the biopsy instrument 10 because the stylet 34 is poised for distal advancement into the tissue to cut a core sample from the tissue and the cannula 32 is poised to distal advancement into the tissue to separate the core sample from the surrounding tissue.

In this configuration, the needle assembly 30 is ready for insertion into the patient. A user can perform the insertion by gripping the front end 22 of the housing 20 between his or her index and forefinger and gently manipulating and advancing the needle assembly 40 through any tissue that needs to be penetrated to reach the target tissue from which the biopsy is to be taken. The user can grip the biopsy instrument 10 in this manner while advancing the instrument 10 to the desired depth within the tissue and/or patient.

Once the needle assembly is positioned at the target site in the tissue, the user can initiate isolation of the tissue sample by advancing the support shaft 40 distally along the longitudinal axis, i.e., in the direction represented by the arrow. To accomplish this movement, the user can depress the plunger head 47 of the support shaft 40 using his/or her thumb. As described above, this distal movement of the support shaft 40 forces the stylet 34 to move distally.

FIG. 5D illustrates the biopsy instrument 10 in a fourth configuration. In this configuration, distal advancement of the plunger head 47 and the movement of the support shaft 40 from the retracted position to the chambered position has continued. As a result, the distal advancement of the stylet 34 has continued such that the distal end of the stylet 38 extends axially beyond the distal end of the cannula 32 and into the target tissue. As a result of this relative movement between the distal end of the stylet 34 and the distal end of the cannula 32, and the resulting relative positioning of the distal end of the cannula 32 and the distal end 38 of the stylet 34, the specimen notch 39 is partially exposed in this configuration and a core sample of the tissue (not illustrated in the Figures) is disposed in the specimen notch 39.

FIG. 5E illustrates the biopsy instrument 10 in a fifth configuration. In this configuration, distal advancement of the plunger head 47 and the movement of the support shaft 40 from the retracted position to the chambered position has continued beyond that achieved in the fourth configuration illustrated in FIG. 5D. As a result, the distal advancement of the stylet 34 has also continued, and the distal end of the stylet 38 extends axially beyond the distal end of the cannula 32 and into the target tissue to a greater extent than that achieved in the fourth configuration illustrated in FIG. 5D. In this configuration, the specimen notch 39 is fully exposed and the complete core sample is disposed in the specimen notch 39.

FIG. 5F illustrates the biopsy instrument 10 in a fifth configuration. In this configuration, the firing trigger 44 has been depressed and, as a result, the cutting cannula 32 has been advanced distally relative to the stylet 34 such that it again surrounds the stylet 34. In this configuration, the cannula 32 surrounds the core sample disposed in the specimen notch 39 and the cutting edge defined by the distal end of the cannula has separated the core sample from the surrounding tissue. Once the biopsy instrument 10 is in this configuration, the instrument 10 can be withdrawn from the tissue and the core sample can be removed from the specimen notch 39 for further processing.

FIGS. 6A, 6B, 6C, and 6D illustrate an internal assembly 100 of the biopsy instrument 10 illustrated in FIG. 1. The internal assembly 100 is illustrated in various configurations that are adopted during use of the biopsy instrument.

The internal assembly 100 includes a first spring 110 that is fixedly attached to a cannula support 112 at a first end 114 and a shaft support 116 at the second end 118. The cannula support 112 defines a housing 120 that surrounds the cutting cannula 32 and to which the first end 114 of the first spring 110 is attached. The shaft support 116 is disposed within a chamber 122 defined by the support shaft 40 and also advantageously surrounds the cutting cannula 32.

The cannula support 112 defines a key 124 that projects downward relative to the cannula 32. Advantageously, the key 124 defines a first surface 126 that lies in a plane that is substantially perpendicular to a longitudinal axis of the cannula 32 and a second surface 128 that lies in a plane that non-orthogonally intersects the longitudinal axis of the cannula 32.

The internal assembly 100 includes a second spring 130 that is fixedly attached to an internal portion of the housing (not illustrated in FIG. 6A, 6B, 6C, or 6D) or a support member connected to the housing at a first end 132 and to the priming slider 42 at a second end 134. Advantageously, the second spring 130 is attached to a key 136 defined by the priming slider 42 that projects downward, into a channel 138 defined by the support shaft 40.

The internal assembly 100 includes a catch 150 that is fixedly attached to an internal portion of the housing or a support member connected to the housing at a first end 152. The second end 154 defines a key 156 that projects upward relative to the cannula 32. Advantageously, the key 156 defines a first surface 158 that lies in a plane that non-orthogonally intersects the longitudinal axis of the cannula 32 and a second surface 160 that lies in a plane that is substantially perpendicular to a longitudinal axis of the cannula 32. Also advantageously, the plane containing the first surface 158 advantageously intersects the longitudinal axis of the cannula 32 at the same angle at which the plane containing the second surface 128 of key 124 intersects the longitudinal axis of the cannula 32.

Figure 6A:
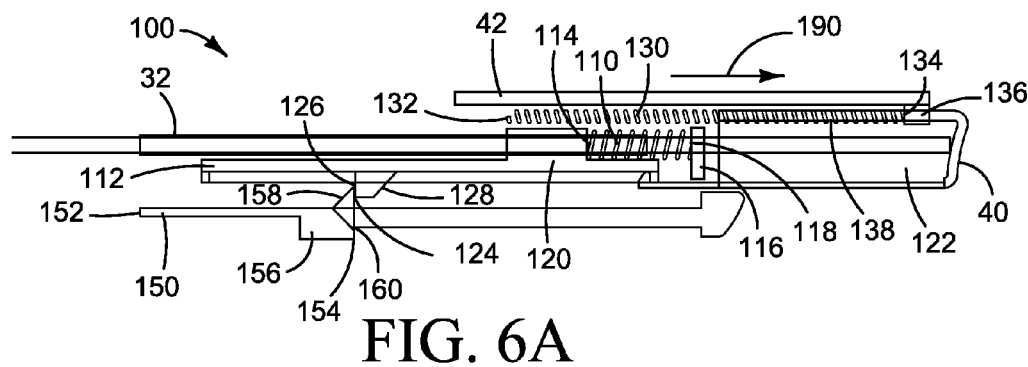
FIG. 6A is a side view of an internal assembly of the biopsy instrument illustrated in FIG. 1. The internal assembly is illustrated in a first configuration.

FIG. 6A illustrates the internal assembly 100 in a first configuration. Priming slider 42 has been moved in the direction of arrow 190 into its second position, extended along the longitudinal axis of and away from the body of the biopsy instrument (not illustrated in FIG. 6A). As a result of this movement, key 136 forces support shaft 40 to also move in the direction of arrow 190 until it reaches its retracted position. The first spring 110 has been compressed and the second spring 130 has been extended. The key 124 of the cannula support 112 has engaged and slid past the key 156 of the catch 150. The mating ramped first surface 126 of the cannula support 112 and the ramped first surface 158 of the catch allow this movement. As illustrated in FIG. 6A, after the key 124 of the cannula support 112 has slid past the key 156 of the catch 150, the second surface 128 of the cannula support 112 and the second surface 160 of the catch are in contact with each other, and prevent return movement of the cannula support 112 despite the force applied to it by compressed first spring 110.

Figure 6B:
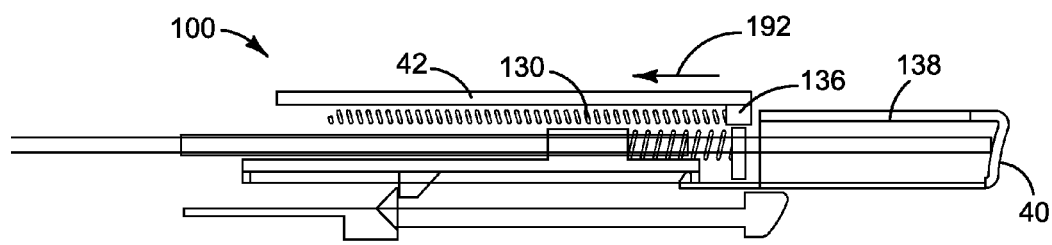
FIG. 6B is a side view of an internal assembly of the biopsy instrument illustrated in FIG. 1. The internal assembly is illustrated in a second configuration.

FIG. 6B illustrates the internal assembly 100 in a second configuration. In this configuration, the user has released the priming slider 42. Second spring 130, which was expanded due to the movement discussed above, recompresses, forcing the priming slider 42 to move in the direction of arrow 192 from its second position and back to its first position over the body of the biopsy instrument (not illustrated in FIG. 6B). Support shaft 40 is not affected by this movement, and stays in its retracted position. During the return movement of the priming slider, key 136 moves through channel 138 defined by the support shaft 40.

Figure 6C:
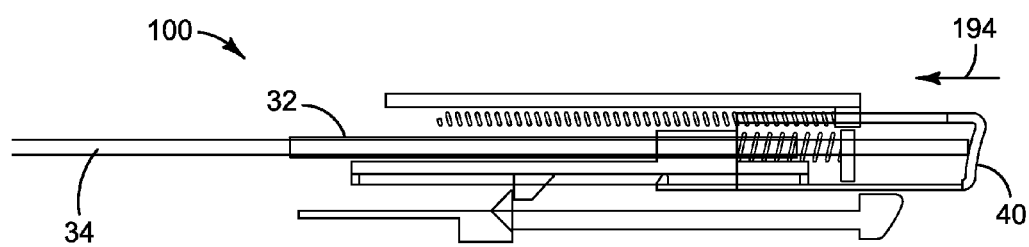
FIG. 6C is a side view of an internal assembly of the biopsy instrument illustrated in FIG. 1. The internal assembly is illustrated in a third configuration.

FIG. 6C illustrates the internal assembly 100 in a third configuration. In this configuration, the support shaft 40 has been advanced along the longitudinal axis of and toward the body of the biopsy instrument (not illustrated in FIG. 6C) in the direction of arrow 194. As a result of this movement, the stylet 34 is advanced through the cannula 32, effectively exposing the specimen notch (not illustrated in FIG. 6C) as described above.

Figure 6D:
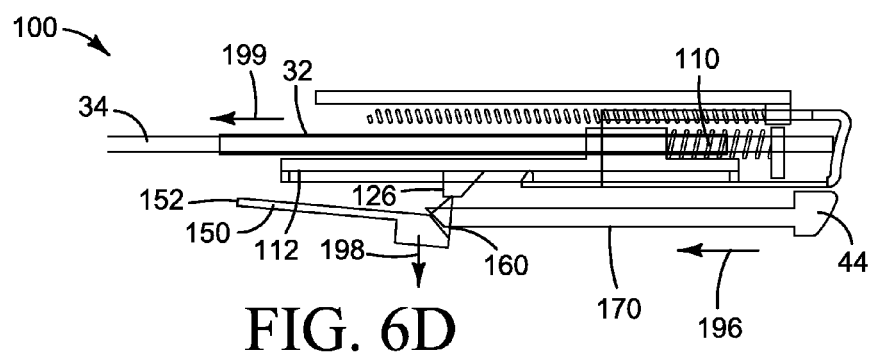
FIG. 6D is a side view of an internal assembly of the biopsy instrument illustrated in FIG. 1. The internal assembly is illustrated in a fourth configuration.

FIG. 6D illustrates the internal assembly 100 in a fourth configuration. In this configuration, the firing trigger 44 has been depressed, moving trigger body 170 in the direction of arrow 196. The trigger body 170 engages catch 150 and, because the first end 152 of catch 150 is fixedly attached to an internal portion of the housing or a support member connected to the housing, the catch 150 deflects downward in the direction of arrow 198. This downward movement of catch 150 slides the second surface 160 of catch 150 past the first surface 126 of cannula support 112 until the two surfaces 160, 126 disengage from their contact with each other. Once this disengagement occurs, the compressive force placed on the first spring 110 is released, forcing the cannula support 112 and the fixedly attached cannula 32 to suddenly move forward in the direction of arrow 199. As a result of this movement, cutting cannula 32 has been advanced distally relative to the stylet 34 such that it again surrounds the distal end of the stylet 34. In this configuration, the cannula 32 surrounds the core sample disposed in the specimen notch (not illustrated in FIG. 6D) and the cutting edge defined by the distal end of the cannula 32 has separated the core sample from the surrounding tissue, as described above.

The foregoing detailed description provides exemplary embodiments of the invention and includes the best mode for practicing the invention. The description and illustration of these embodiments is intended only to provide examples of the invention, and not to limit the scope of the invention, or its protection, in any manner.

I claim:

1. A biopsy instrument, comprising:
   a housing having a front end opposite a rear end and a housing length extending between the front end and the rear end, the housing having a first longitudinal axis extending along the housing length and defining an inner passageway;
   a needle assembly extending from the front end of the housing, the needle assembly having a proximal end disposed in the inner passageway and a distal end, the needle assembly comprising a cannula defining a lumen and a stylet having a distal end defining a specimen notch, the stylet slidably disposed within the lumen;
   a support shaft having a first end and a second end and moveable between a chambered position in which the entire circumference of the first end and the entire circumference of a first axial portion of the support shaft extending a first distance from the first end toward the second end are disposed entirely within the inner passageway and a retracted position in which the support shaft is retracted from the inner passageway such that the entire circumference of the first end and the entire circumference of a second axial portion of the support shaft extending a second distance from the first end toward the second end are disposed entirely within the inner passageway, the second distance less than the first distance, the support shaft operably connected to the stylet and the cannula such that proximally-directed movement of the support shaft from the chambered position to the retracted position and along the first longitudinal axis produces proximally-directed movement of the stylet and the cannula along the first longitudinal axis, and such that distally-directed movement of the support shaft from the retracted position to the chambered position and along the first longitudinal axis produces distally-directed movement of the stylet;
   a handle connected to the housing and extending away from the housing, the handle having a second longitudinal axis that intersects the first longitudinal axis at an acute angle; and
   a priming slider connected to the housing and adapted to move from a first position to a second position such that movement of the priming slider from the first position to the second position results in movement of the support shaft from the chambered position to the retracted position, in the first position the priming slider is disposed over the housing and in the second position the priming slider extends along the first longitudinal axis and away from the rear end of the housing.

2. The biopsy instrument of claim 1, wherein the priming slider is biased toward the first position.

3. The biopsy instrument of claim 1, further comprising a firing trigger disposed adjacent the second end of the support shaft;
   wherein the cannula is moveable from a spring biased position to a sampling position; and
   wherein depression of the firing trigger releases the cannula from its spring biased position and advances the cannula along said stylet.

4. The biopsy instrument of claim 1, further comprising a gripping portion disposed on the front end of the housing and configured for grasping by an operator of said surgical cutting instrument.

5. The biopsy instrument of claim 1, wherein the angle comprises an angle greater than about 0° and less than about 90°.

6. The biopsy instrument of claim 1, wherein the angle comprises an angle greater than about 40° and less than about 85°.

7. The biopsy instrument of claim 1, wherein the angle comprises an angle greater than about 45° and less than about 80°.

8. The biopsy instrument of claim 1, wherein the angle comprises an angle greater than about 50° and less than about 75°.

9. The biopsy instrument of claim 1, wherein the angle comprises an angle greater than about 55° and less than about 75°.

10. The biopsy instrument of claim 1, wherein the angle comprises an angle greater than about 60° and less than about 75°.

11. The biopsy instrument of claim 1, wherein the angle comprises an angle greater than about 60° and less than about 70°.

12. The biopsy instrument of claim 1, wherein the angle comprises an angle of about 55°.

13. The biopsy instrument of claim 1, wherein the angle comprises an angle of about 60°.

14. The biopsy instrument of claim 1, wherein the angle comprises an angle of about 65°.

15. A biopsy instrument, comprising:
   a housing having a front end opposite a rear end and a housing length extending between the front end and the rear end, the housing having a first longitudinal axis extending along the housing length and defining an inner passageway;
   a needle assembly extending from the front end of the housing, the needle assembly having a proximal end disposed in the inner passageway and a distal end, the needle assembly comprising a cannula defining a lumen and a stylet having a distal end defining a specimen notch, the stylet slidably disposed within the lumen;
   a support shaft having a first end and a second end and moveable between a chambered position in which the entire circumference of the first end and the entire circumference of a first axial portion of the support shaft extending a first distance from the first end toward the second end are disposed entirely within the inner passageway and a retracted position in which the support shaft is retracted from the inner passageway such that the entire circumference of the first end and the entire circumference of a second axial portion of the support shaft extending a second distance from the first end toward the second end are disposed entirely within the inner passageway, the second distance less than the first distance, the support shaft operably connected to the stylet and the cannula such that proximally-directed movement of the support shaft from the chambered position to the retracted position and along the first longitudinal axis produces proximally-directed movement of the stylet and the cannula along the first longitudinal axis, and such that distally-directed movement of the support shaft from the retracted position to the chambered position and along the first longitudinal axis produces distally-directed movement of the stylet;
   a priming slider connected to the housing and the support shaft, the priming slider adapted to move from a first position to a second position such that movement of the priming slider from the first position to the second position results in movement of the support shaft from the chambered position to the retracted position, in the first position the priming slider is disposed over the housing and in the second position the priming slider extends along the first longitudinal axis and away from the rear end of the housing; and
   a handle connected to the housing and extending away from the housing, the handle having a second longitudinal axis that intersects the first longitudinal axis at an angle greater than about 40° and less than about 85°.

16. The biopsy instrument of claim 15, wherein the angle comprises an angle greater than about 50° and less than about 75°.

17. The biopsy instrument of claim 15, wherein the angle comprises an angle greater than about 55° and less than about 75°.

18. The biopsy instrument of claim 15, wherein the angle comprises an angle greater than about 60° and less than about 75°.

19. A biopsy instrument, comprising:
   a housing having a front end opposite a rear end and a housing length extending between the front end and the rear end, the housing having a first longitudinal axis extending along the housing length and defining an inner passageway;
   a needle assembly extending from the front end of the housing, the needle assembly having a proximal end disposed in the inner passageway and a distal end, the needle assembly comprising a cannula defining a lumen and a stylet having a distal end defining a specimen notch, the cannula moveable from a spring biased position to a sampling position, the stylet slidably disposed within the lumen;
   a support shaft having a first end and a second end and moveable between a chambered position in which the entire circumference of the first end and the entire circumference of a first axial portion of the support shaft extending a first distance from the first end toward the second end are disposed entirely within the inner passageway and a retracted position in which the support shaft is retracted from the inner passageway such that the entire circumference of the first end and the entire circumference of a second axial portion of the support shaft extending a second distance from the first end toward the second end are disposed entirely within the inner passageway, the second distance less than the first distance, the support shaft operably connected to the stylet and the cannula such that proximally-directed movement of the support shaft from the chambered position to the retracted position and along the first longitudinal axis produces proximally-directed movement of the stylet and the cannula along the first longitudinal axis, and such that distally-directed movement of the support shaft from the retracted position to the chambered position and along the first longitudinal axis produces distally-directed movement of the stylet;
a priming slider connected to the housing and the support shaft, the priming slider adapted to move from a first position to a second position such that movement of the priming slider from the first position to the second position results in movement of the support shaft from the chambered position to the retracted position, in the first position the priming slider is disposed over the housing and in the second position the priming slider extends along the first longitudinal axis and away from the rear end of the housing;
a firing trigger, wherein depression of the firing trigger releases the cannula from its spring biased position and advances the cannula along said stylet;
a gripping portion disposed on the front end of the housing and configured for grasping by an operator of said biopsy instrument; and
a handle connected to the housing and extending away from the housing, the handle having a second longitudinal that intersects the first longitudinal axis at an angle greater than about 50° and less than about 75°.

* * * * *